United States Patent
Duran (10) Patent No.: US 10,458,936 B2
(45) Date of Patent: Oct. 29, 2019

(54) APPARATUS AND METHOD FOR THE DETERMINATION OF THE ABSOLUTE COEFFICIENT OF THERMAL EXPANSION IN ULTRALOW EXPANSION MATERIALS

(71) Applicant: Corning Incorporated, Corning, NY (US)

(72) Inventor: Carlos Alberto Duran, Ottawa (CA)

(73) Assignee: Corning Incorporated, Corning, NY (US)

( * ) Notice: Subject to any disclaimer, the term of this patent is extended or adjusted under 35 U.S.C. 154(b) by 235 days.

(21) Appl. No.: 15/493,944

(22) Filed: Apr. 21, 2017

(65) Prior Publication Data

US 2017/0328848 A1 Nov. 16, 2017

Related U.S. Application Data

(60) Provisional application No. 62/334,569, filed on May 11, 2016.

(51) Int. Cl.
| | |
|---|---|
| *G01K 1/00* | (2006.01) |
| *G01N 25/00* | (2006.01) |
| *G01N 25/16* | (2006.01) |
| *G03F 7/20* | (2006.01) |
| *G01N 33/38* | (2006.01) |

(52) U.S. Cl.
CPC ........... *G01N 25/16* (2013.01); *G01N 33/386* (2013.01); *G03F 7/70958* (2013.01)

(58) Field of Classification Search
USPC .................................. 374/55, 208, 120, 187
See application file for complete search history.

(56) References Cited

U.S. PATENT DOCUMENTS

| | | | | |
|---|---|---|---|---|
| 5,296,374 A | * | 3/1994 | Culshaw | G01K 5/52 374/117 |
| 6,687,008 B1 | | 2/2004 | Peale | |
| 7,239,397 B2 | | 7/2007 | Badami | |

(Continued)

FOREIGN PATENT DOCUMENTS

| | | |
|---|---|---|
| CN | 201141843 Y | 10/2008 |
| JP | 2002107318 A | 4/2002 |
| KR | 875489 B1 | 12/2008 |

OTHER PUBLICATIONS

J.W. Berthold III and S.F. Jacobs, "Ultraprecise thermal expansion measurements of seven low expansion materials", Applied Optics, vol. 5, 10, pp. 2344-2347, (1976).

(Continued)

*Primary Examiner* — Mirellys Jagan
(74) *Attorney, Agent, or Firm* — John P. McGroarty (57) ABSTRACT

An improved method and apparatus for determination of the absolute coefficient of thermal expansion of materials, including ultralow expansion materials, utilizes a metrology frame that is regulated within a first narrow temperature range that varies by only a small fraction of a degree Celsius from a set point temperature (e.g., less than about 0.01° C. from the set point temperature), while the temperature of the sample is varied to determine the coefficient of thermal expansion over a larger temperature range (e.g., 30, 40 or 50° C.). The method and apparatus permit determination of the coefficient of thermal expansion of a material to levels approaching $10^{-9}/°$ C.

12 Claims, 6 Drawing Sheets

(56) References Cited

U.S. PATENT DOCUMENTS

| | | | |
|---|---|---|---|
| 7,426,039 B2 | 9/2008 | Badami | |
| 7,471,396 B2* | 12/2008 | Jansen | G01B 11/06 |
| | | | 356/492 |
| 7,808,647 B2* | 10/2010 | Lehmann | G01B 11/2441 |
| | | | 356/489 |
| 8,328,417 B2 | 12/2012 | Duran | |
| 2006/0132794 A1 | 6/2006 | Badami et al. | |

OTHER PUBLICATIONS

Henry E. Hagy, "High Precision Photoelastic and Ultrasonic Techniques for Determining Absolute and Differential Thermal Expansion of Titania-Silica Glasses", Applied Optics, vol. 12, Issue 7, pp. 1440-1446, (1973).

H.E. Hagy and W.D. Shirkey, "Determining absolute thermal expansion of titania-silica glasses: a refined ultrasonic method", Applied Optics, vol. 14, Issue 9, pp. 2099-2103, (1975).

V.G. Badami and M. Linder, "Ultra-High Accuracy Measurement of the Coefficient of Thermal Expansion for UltraLow Expansion Materials", Proc. SPIE, vol. 4688, pp. 469-480 (2001).

Bennett, "An Absolute Interferometric Dilatometer" J. Phys. E: Sci Instrum 10, 525-530, 1977.

Hrdina et al. "Measuring and Tailoring CTE within ULE® Glass" Proc. SPIE 5037(227-235) 2003.

International Search Report and Written Opinion PCT/US2017/031693 dated Jul. 5, 2017.

Okaji et al. "A practical measurement system for the accurate determination of linear thermal expansion coefficients" J Phys E: Sci Instrum 17 (669-673) 1984.

Okaji et al. "High-resolution multifold path interferometers for dilatometric measurements" J Phys E: Sci Instrum 16 (1983) pp. 1208-1213.

Okaji et al. "Laser interferometric dilatometer at low temperatures: application to fused silica SRM 739" Cryogenics 35, 887-891 (1995).

Roberts, "Absolute dilatometry using polarization interferometer" J. Phys. E: Sci. Instrum. 14(12), pp. 1386-1388, 1981.

Spannagel et al. "CTE measurement setup with 10ppb/K sensitivity for characterizing lightweight and highly stable materials for space applications" Optomechatronic Micro/Nano Devices and Components III: 8-10, 2007, vol. 8450, pp. 84500Q-1-84500Q-7.

Takeicha et al. "High-precision optical heterodyne interferometric dilatometer for determining absolute CTE of EUVL materials" Proceedings SPIE vol. 5751, p. 1069-1076 (2005).

* cited by examiner

APPARATUS AND METHOD FOR THE DETERMINATION OF THE ABSOLUTE COEFFICIENT OF THERMAL EXPANSION IN ULTRALOW EXPANSION MATERIALS

This application claims the benefit of priority under 35 U.S.C. § 119 of U.S. Provisional Application Ser. No. 62/334,569 filed on May 11, 2016 the content of which is relied upon and incorporated herein by reference in its entirety.

FIELD OF THE DISCLOSURE

This disclosure pertains to an apparatus and method for determining the coefficient of thermal expansion of materials, including materials that exhibit very small dimensional changes with temperature, and more particularly to such apparatus and method that more effectively thermally isolate the apparatus from the sample being tested.

BACKGROUND OF THE DISCLOSURE

Mirror substrates for use in projection optics systems within extreme ultraviolet (EUV) lithography (EUVL) scanners must meet stringent thermal expansion requirements in order to maintain their intended surface shape (known as "figure") upon temperature changes caused by normal operation cycles of the scanner. For this reason, the preferred material for manufacturing state of the art projection optics mirror substrates is Ultra Low Expansion glass (ULE® Glass), manufactured by Corning Incorporated. Glass sold by Corning Inc. under the glass code 7973 is specifically tuned for EUVL applications, and is characterized by high degrees of precision and accuracy, which permit supplying glass with properties that are narrowly targeted to each specific application.

As the EUVL source power increases to meet the requirements of a high volume manufacturing system, the thermal expansion specifications for the projection optics mirror substrates are becoming tighter. For example, the maximum allowable CTE (coefficient of thermal expansion) slope, the rate of change of CTE with temperature, which is 1.6 ppb/K$^2$ at 20° C. for standard ULE® is expected to decrease below 1.0 ppb/K$^2$. Taking full advantage of the better performance enabled by low slope materials requires improved material uniformity and more precise knowledge of the Tzc (zero crossover temperature), the temperature at which the CTE is equal to zero.

Tzc in ULE® glass is controlled by composition and by the thermal history of the glass. Qualification of production ULE® glass to ensure that it fulfills specification requirements for Tzc involves measurements of CTE using an indirect acoustic method. The method has been successful so far, but it has some shortcomings. It relies on the material having a well-defined thermal history. Measuring material with different thermal history requires the calibration to be corrected for the specific thermal history. There is potential for uncontrolled factors, such as hydroxyl (—OH) content, affecting the calibration and going unnoticed, which would introduce errors in the Tzc calculated for the part. Efforts to correlate the technique to absolute dilatometry show a residual error in the order of 1 to 2° C. in the zero crossover temperature calculated for the parts. Due to its indirect nature, and its reliance on an empirical calibration, makers of EUVL scanners are uncomfortable relying on its results for qualifying material when requirements for Tzc accuracy are in the order of a few degrees C.

On the other hand, the value of Tzc can be ascertained by measuring a sample of glass in an absolute dilatometer, including a Fabry-Perot interferometer (FPI). Absolute FPI dilatometry is a well established technique, but it is not suitable for controlling glass in a production environment. It requires carefully finished samples, which are expensive and take a long time to manufacture (4 to 8 weeks). It requires expensive specialized equipment and highly skilled personnel. It is potentially affected by subtle and hard-to-quantify effects such as temperature dependence of reflection coatings, and the quality of optically contacted bonds. A high resolution measurement requires use of "end caps" preferably made of the same material under evaluation. These ends caps are required to be transparent, meaning that only optically clear materials can be measured at the highest resolution. Due to the relatively large size of the needed samples (100 grams or more), it is sometimes difficult to select a sample that truly represents the material in a part. It is slow, typically taking a week or more to measure a sample. The slow speed, together with the complexity of measurement setup and sample requirements, makes this technique very expensive and severely restricts its use.

Badami and Patterson proposed methods for highly accurate measurements of dimensional changes in commonly-owned U.S. Pat. Nos. 7,239,397 and 7,426,039. These methods are able to measure dimensional changes with high precision on monolithic samples. However, the instruments are highly specialized and complex, and it was not demonstrated that they can reliably measure CTE(T) with the required precision and accuracy.

A highly complex Optical Heterodyne Interferometric Dilatometer for determination of absolute CTE of EUVL materials has been demonstrated by Takeicha et al. (Proceedings SPIE vol. 5751, p 1069 (2005) and vol. 6151 p 61511Z-2 (2006). The apparatus relies on expensive components such as a frequency-stabilized laser. The method relies on mechanical contact between a sample and a reference surface, subjecting the measurement to potential errors that are difficult to quantify. Furthermore, it was not demonstrated that the technique is capable of measuring the thermal expansion behavior with the required accuracy over a wide temperature range.

Various other methods involve mechanical contact between one end of the sample and a reference surface, introducing a source of uncertainty that is hard to quantify.

The photoelastic sandwich seal technique can be used to measure the difference in CTE between samples of two materials using much simpler and faster equipment than absolute dilatometry, but it has shortcomings of its own. It also requires relatively expensive and carefully made samples, with a long lead time. It measures differences in CTE between two materials, and not directly the absolute CTE or Tzc. Establishing absolute Tzc requires correlation to a reference. Its ultimate resolution in establishing the absolute CTE of a sample is 3 to 5 times less accurate than needed for high-end applications such as critical mirrors in EUVL projection systems. Due to these reasons, the technique is not well suited for direct Tzc characterization in a production environment.

Interferometry has been shown to be useful in providing maps of variations of CTE, and thus Tzc in ULE® glass. Refractive index variations correlate to TiO$_2$ concentration variations, which in turn correlate to CTE. Interferometry maps exhibit the highest resolution of any technique both spatially and in CTE (in the range of parts per trillion), but do not provide information about the absolute values of the CTE.

A photoelastic method for determining the zero crossover of the CTE(T) curve in ULE® glass was proposed by the present inventor in commonly-owned U.S. Pat. No. 8,328,417. That method has the distinct advantage of not requiring an optically contacted sample or complex and expensive laser systems, but it only aims to measure the zero crossover temperature, and can only marginally give information on the temperature dependence of CTE(T). Further, the samples needed for the measurement are bulkier than required by the present invention, and thus require longer stabilization times.

Thus, there is an unmet need for a technique that allows quick and inexpensive measurement of the absolute CTE(T) of a small sample of ULE® glass, without the need for expensive equipment or samples that have high cost and take a long time to manufacture. Furthermore, such an invention could be used in production to provide an absolute reference for relative index measurements carried out using interferometry, which would allow this higher resolution technique to replace highly labor intensive, lower spatial resolution ultrasonic velocity measurements.

In a broader context, measurements of the coefficient of thermal expansion for ultra-low expansion material are difficult to carry out, since they involve measuring displacements on the nanometer (nm) scale on macroscopic samples measuring in the order of 10 mm or more. This level of performance cannot be achieved using commercial dilatometers, which in most cases involve mechanical contact between a sample and a mechanical sensor or a reference surface. Even high-quality commercial dilatometers based on optical interference measurement principles, such as instruments manufactured by Rigaku and Linseis, are susceptible to thermally induced drifts in the order of tens of nanometers, rendering them of little value for evaluating ultralow expansion materials with CTE values on the order of $10^{-9}/°$ C. (1 ppb/K).

SUMMARY OF THE DISCLOSURE

A high-resolution dilatometer able to measure the temperature-dependent coefficient of thermal expansion on small and monolithic samples of ultralow expansion materials is disclosed. The dilatometer disclosed herein is a fully non-contact optical system that employs commercially available, high resolution interferometric sensors to detect the positions of the two ends of the sample under examination. The high resolution sensors are mounted on a temperature-regulated measurement frame, constructed of an ultralow expansion material, such as ULE® glass made by Corning Incorporated. In a high-resolution configuration, the instrument measures a multiplicity of points on at least one of the sample ends to detect potential rotation or deformation of the sample during the measurement, and enable correction of spurious effects for maximum resolution. In a standard configuration, the position of each end of the sample is detected using a single detector. The measurement can be conducted in high vacuum, at a pressure lower than $10^{-6}$ bar (1 microbar), in order to avoid atmospheric refraction effects on the optical distance measurement and to enable high thermal stability of the measurement device.

The apparatus described herein provides a compact structure able to measure the absolute thermal expansion of materials with low to ultra-low expansion (on the order of $10^{-9}/°$ C.) on a small sample (3 to 5 cm$^3$) that can be manufactured inexpensively. No commercial dilatometer on the market is able to perform these measurements, while high-end, one-of-a-kind instruments usually involve large, complex and expensive systems that require samples with a volume typically 50 cm$^3$ or larger, requiring expensive and specialized preparation. These dedicated instruments usually require one or more high-end laser systems and the associated optical layout. In some cases, they also require a rather large volume to be placed in an evacuated chamber. Finally, their size renders them sensitive to external vibrations, requiring the use of vibration isolation equipment, which increases the complexity and cost of the system.

The technique presented here can use samples that are small, easy and inexpensive to manufacture (for example a slab measuring 35 mm×20 mm×4 mm, or approximately 1.4"×0.8"×0.16"). This is a substantial advantage when compared to any other technique capable of determining Tzc at comparable levels of precision and accuracy. There are no requirements on the optical properties of the materials that can be measured using the present invention. Other techniques require samples to be optically clear, or they require the use of materials with specific optical properties that are also well matched in thermal expansion properties to the material to be measured. The small size of the sample allows for rapid thermal stabilization, allowing for faster measurement turnaround and/or extended measurement range compared to dedicated instruments in the $10^{-9}/°$ C. class.

The technique itself is simple, fast, and sufficiently economic to lend itself to routine use in the glass manufacturing plant. Such use can dramatically reduce problems associated with shipping parts with Tzc outside of specification. The technique obviates the need of producing samples to be measured by an FPI-dilatometer. The cost of producing the small slabs needed by the present technique is significantly lower (estimated cost is a maximum of ¼ of the cost of finishing an FPI "spacer"). The small slabs consume a volume of material about an order of magnitude smaller than the FPI spacers. Further, the technique is capable of handling a variety of sample shapes.

Commercial dilatometers currently available are fully capable of measuring thermal expansion in materials with CTE down to $10^{-6}/°$ C. Some higher-end systems are able to measure reliably down to ~$10^{-7}/°$ C. or slightly below. No commercial instruments are capable of measuring samples with CTE ~$10^{-8}/°$ C. or lower, a need only partially met by specially built, expensive equipment using large samples requiring specialized preparation. The disclosed apparatus and method enables measurements into the $10^{-9}/°$ C. range using a compact configuration at a lower cost and on significantly smaller and simpler samples.

DETAILED DESCRIPTION

The semiconductor industry produces the silicon chips that have fueled the information revolution taking place during the late 20$^{th}$ and early 21$^{st}$ centuries. The industry has succeeded in this enterprise by continuously improving the performance of semiconductor chips while simultaneously reducing their manufacturing cost. This has been achieved by means of ever increasing the optical resolution of the cornerstone piece of equipment in the semiconductor fabrication, the lithography scanner, which has enabled production of chips with ever shrinking feature sizes. The endeavor for higher resolution has resulted in the reduction of the operating wavelength of the scanners, which has reached the limit practically attainable using traditional, refractive optics at the current wavelength of ~193 nm, generated by ArF excimer lasers. ArF scanners are about to reach the smallest feature sizes that they are capable of achieving, meaning that the industry needs to find a new technology if it is to continue to increase the density of components within integrated circuits. The most likely candidate to replace optical lithography when this technique reaches the limit of its technical capability is extreme ultraviolet lithography (EUVL). Several pilot-line EUVL tools are currently in operation, and it is expected that chip production using this technology will start in a few years from now. Production-capable EUVL tools are in the design stage at this time. One key difference between current, pilot-line tools, and production tools, is the much higher light source intensity required by the latter in order to fulfill production throughput requirements.

EUVL is similar to current optical lithography in that it relies on an optical projection system to reproduce features from a master reticle (also known as mask) onto a thin photosensitive layer (resist) deposited on the surface of a semiconductor wafer. EUVL operates at a wavelength of ~13.4 nm, at which no known material is transparent. Thus, the EUVL projection system needs to be built based on reflective components (mirrors) rather than refractive elements (lenses). The extremely short wavelength of the radiation poses a number of challenges to the EUVL system designers. For example, reflective coatings on the mirrors are fundamentally limited to ~70% efficiency, implying that 30% of the radiation is lost at each surface. This radiation is absorbed as heat by the mirror substrate, which causes mirror deformation if the material expands or contracts with temperature changes. Additionally, since all gases absorb 13.4 nm radiation, the system needs to operate in vacuum, making it more difficult to remove heat from the mirrors, and exacerbating the problem of mirror heating. Thus, extremely tight requirements are placed on the materials used to make the mirror substrates to be used in a EUVL system. Currently, Ultra Low Expansion (ULE®) glass, (code 7973) made by Corning is the material of choice for production of EUVL projection mirrors. ULE® glass code 7973 has an extremely low coefficient of thermal expansion (CTE) at room temperature, which is critical in allowing the shape of the mirror to stay constant upon heating. The material also possesses other key properties, such as low striae, which enables the production of very precise mirror surfaces, long term chemical and dimensional stability and compatibility with a vacuum environment.

Figure 1:
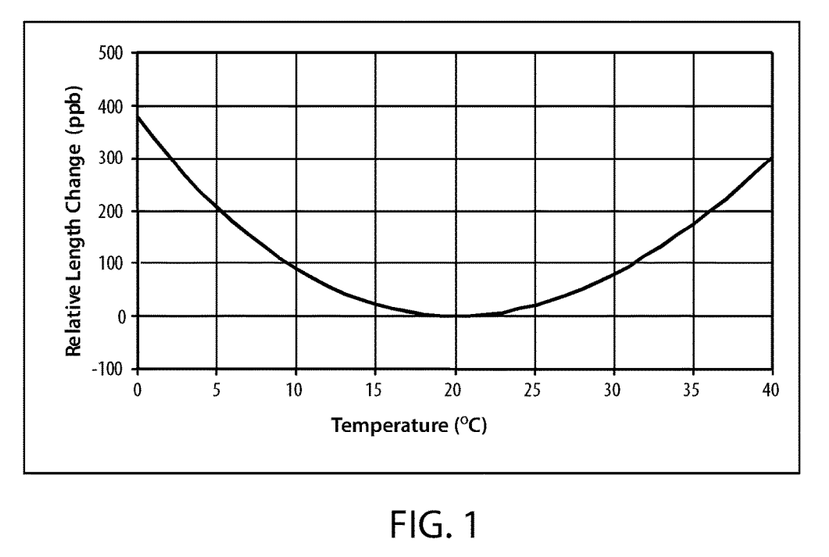
FIG. 1 is a graph showing the temperature dependence of the relative length of a piece of typical ULE® glass, of nominal composition, and annealed using the standard anneal process, wherein at temperatures below ~20° C. the glass shrinks at a rate that decreases with increasing temperature, at a temperature of 20° C. the length of the glass reaches a minimum, and at higher temperatures, its length increases with increasing temperature.

All materials either expand or contract upon changes in temperature. ULE® glass is characterized by extremely small changes in dimensions at temperatures close to room temperature, as seen in FIG. 1. More specifically, the CTE of ULE® glass is zero at a temperature called the "Zero Crossover Temperature", and denoted Tzc (FIG. 2, in which "expansivity" corresponds to CTE). Below that temperature, CTE is negative, and above Tzc, it is positive. Based on calculations of its thermal load, size, and heat removal rates afforded by the system, EUVL system designers calculate an optimum Tzc value for each mirror in the system. This is a critical material parameter, and one that is tightly specified by the optical system designers.

Manufacturers encounter difficulties making glass that will satisfy the tight Tzc requirements, and measuring Tzc with the required precision. The current ultrasonic Tzc measurement method does not enjoy full confidence from EUVL equipment manufacturers, who require additional glass samples made from material that correlates to the material used in the part. These samples are measured using Fabry-Perot interferometry, which between sample preparation and testing take a long time and significantly delay shipment of production material. Results from the ultrasonic technique correlate to Fabry-Perot data with a typical error of between 1° C. and 2° C., which in some cases is in the order of the specification range for Tzc. Discrepancies can arise from several factors, including material selection, sample size limitations from each of the techniques, and uncontrolled factors that may affect the empirical calibration used in the ultrasonic technique. These discrepancies are difficult to quantify and hard to eliminate.

A technique is needed that can measure the temperature dependence of CTE (CTE(T)) directly and economically on a small sample of ULE® glass, allowing immediate verification of Tzc in glass parts, thus significantly reducing lead times, required inventory levels, and potential liability on parts for which FPI measurements are not available. Additionally, the technique would serve to control a post-fabrication annealing process used to fine tune Tzc on individual parts, thus enabling production of parts with Tzc defined within significantly narrower specification ranges. The technique would also be useful in further validating ultrasonic CTE measurements, thus boosting confidence in those results. Further, the technique would enable measurement of CTE(T) of samples of novel ultralow expansion materials, and enable their development. CTE(T) of new materials can thus be characterized in detail even if only small samples are available, thus enabling faster development cycle time than if large samples were requested.

Figure 2:
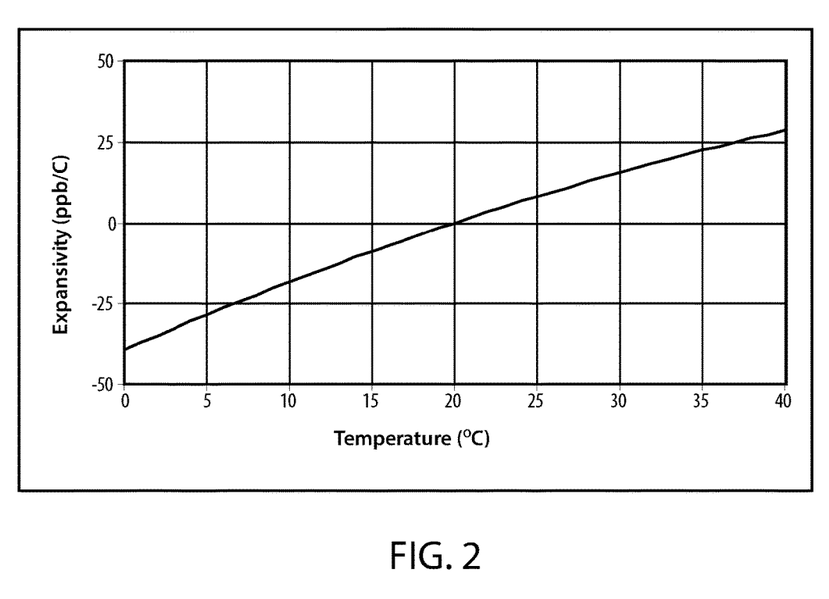
FIG. 2 is a graph showing the rate of change of the relative length (Expansivity α(T)) of the same typical piece of ULE® glass of FIG. 1, wherein the expansivity is negative at low temperatures, and positive at high temperatures, and the temperature at which the expansivity crosses the horizontal axis coincides with the minimum in FIG. 1, called the temperature of zero expansion, or zero crossover temperature, and denoted Tzc.

FIGS. 1 and 2 show the temperature dependence of relative length of a typical ULE® glass, and CTE (which corresponds to the rate of change of relative length with temperature) of a typical ULE® glass, respectively.

Figure 3A:
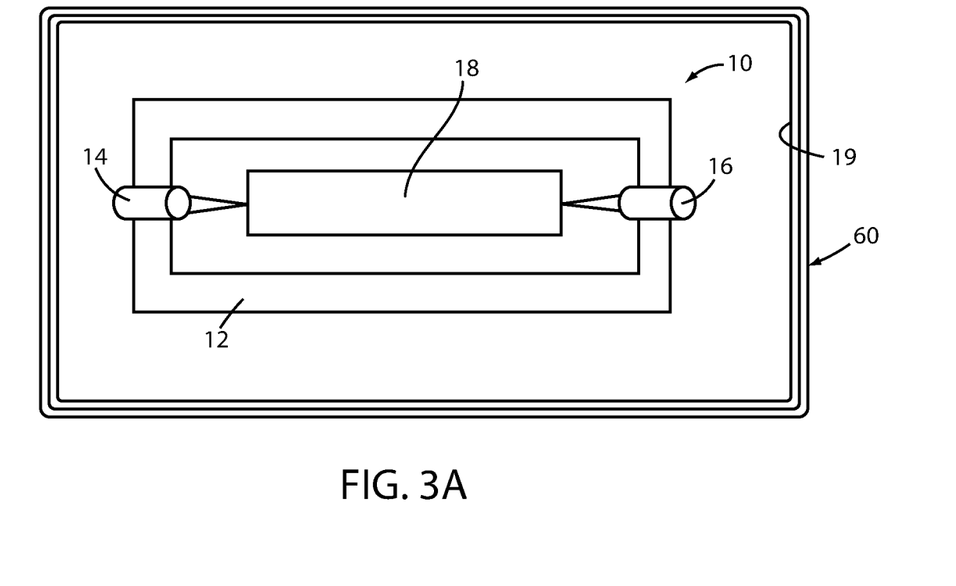
FIG. 3A is a schematic top view of the standard configuration apparatus as disclosed, in which the position sensors are held by a frame made of a low expansion material, such as ultralow expansion ULE® glass made by Corning Incorporated, or another ultralow thermal expansion material such as Zerodur® made by Schott, or ClearCeram® made by Ohara Corporation.

The apparatus 10 (shown in FIG. 3A) consists of a frame 12 which holds a set of position sensors 14, 16 firmly in place. Frame 12 is preferably made from a material having a low coefficient of thermal expansion. In the illustrated embodiment, the frame is made of ULE® glass with a zero crossover temperature Tzc specifically chosen at a convenient value. For example, for measurements of materials in the range close to room temperature, it can be convenient to choose ULE® glass with a Tzc a few degrees higher than room temperature. It is then practically convenient to regulate the temperature of the frame at a temperature very close to the Tzc of its constituent material. Desirably, the temperature of the frame is maintained within a range of about ±0.01° C. of a set point temperature, the set point temperature being within ±5° C. of the Tzc of the frame material. More desirably, the temperature of the frame is maintained within a range of about 0.005° C. of a set point temperature, the set point temperature being within about ±2° C. of the Tzc of the frame material. By doing so, distortions to the frame due to changes in temperature are minimized, and a stable reference is maintained for the measurement of thermal expansion of the sample. Despite use of an ultralow expansion material, excursions in the temperature of the frame from a stable value will result in dimensional changes of the frame, and will thus have a detrimental effect on the measurement process. Stable regulation is facilitated by placing the frame in a high vacuum enclosure 60, thus minimizing thermal exchange by conduction and convection. Preferably, the frame, sample and sensors are all enclosed in an airtight vacuum chamber connected to a vacuum pump. Further improvement in the regulation is achieved by minimizing thermal exchange through radiation by means of appropriate reflective shields 19. In order to achieve maximum stability, care must be taken in minimizing exposure of surfaces of the frame to thermal radiation sources. Frame 12 can be made, for example, of a material having a coefficient of thermal expansion of less than $50 \times 10^{-9}$ $K^{-1}$ at 20° C. or less than $20 \times 10^{-9}$ $K^{-1}$ at 20° C., and a Tzc from 290K to 300K.

In order to perform a thermal expansion measurement, the temperature of the sample 18 needs to be controlled over a temperature range of interest as its changes in length are recorded. In certain embodiments, the temperature range is at least 25 K and the measuring is completed within a period of 25 hours. On one hand, the sample must be held in a stable position with respect to the measurement frame, so that the length measurements can be performed with high resolution, which generally requires a solid mechanical link between the sample and the measurement frame. It is desirable that the sample and the measurement frame are decoupled from a thermal point of view, since it is critical that the frame remains at a stable temperature while the temperature of the sample is varied. To this end, the sample is held in position by a holder whose dual function is mechanical rigidity and thermal isolation. A preferred material choice for the holder is a low thermal conductivity material, such as ULE® glass. This glass is stable mechanically, will result in minimal displacement of the sample as it changes temperature, and its low thermal conductivity results in low losses of heat from the sample into the measurement apparatus. The shape of the holder is engineered to minimize heat exchange while keeping the sample in a stable position.

Figure 3B:
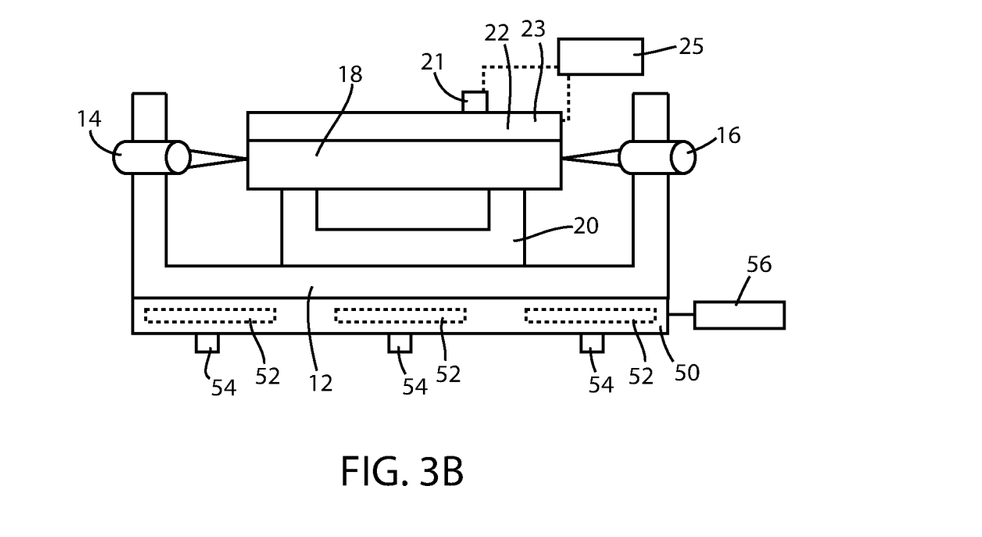
FIG. 3B is a schematic side view of an alternative configuration, showing the sample, the measurement frame holding the position sensors, and the sample holder keeping the sample in place, wherein the material of both holder and frame is ultralow expansion ULE® glass made by Corning Incorporated, or another ultralow expansion material such as Zerodur® made by Schott, or ClearCeram® made by Ohara Corporation, and the sample block is made of a good thermal conductor and contains heating elements and temperature sensors.

In the illustrated embodiment (FIG. 3B), the sample holder 20 rests directly on the bottom section of the measurement frame, is made of the same material as the frame 12, and is prevented from sliding off by means of a thin layer of vacuum grease or a similarly viscous compound between the flat bottom of the holder and the top surface of the lower section of the measurement frame. In FIG. 3B, both the measurement frame 12 and the sample holder 20 are shown as being shaped as a letter "U": in the case of the frame, the side bars of the "U" hold the sensors, while the bottom provides support for the sample holder; in the case of the holder, the tops of the side bars of the "U" are finished flat and parallel to the bottom surface of the holder, so that the sample 18 is kept in a stable position with its length parallel to the horizontal plane.

A small amount of a viscous compound can be used in between the holder top and the sample bottom, mainly to minimize unwanted motion of the sample. A sample block 22 is provided resting above the sample 18. The sample block 22 is preferably manufactured out of a high thermal conductivity material, such as aluminum, copper or other metal, in order to ensure effective control of a uniform temperature distribution throughout the sample. Also provided are electrical heaters 23 within the sample block 22 to allow changing the sample temperature, as well as one or more temperature sensors 21, such as platinum resistive sensors for measurement and control purposes. A controller 25 is used to regulate the electrical heaters in response to the measured temperature. Preferably, a thin layer of high thermal conductivity viscous compound is provided between the sample and sample block, to ensure intimate thermal contact between the two. It is highly desirable that this interfacial compound remains viscous throughout the whole measurement process. If at some point it were to become rigid, it would subject the sample to mechanical stress from thermal expansion in the sample block, potentially resulting in loss of accuracy in the measurements.

The sample 18 can be prepared in a shape such that its vertical thickness is on the order of at least 5 times smaller than its lateral dimensions, in order to ensure temperature uniformity throughout. The lateral dimensions of the sample block 22 can be the same as those of the sample or alternatively somewhat larger. A sample block smaller than the lateral dimensions of the sample, although not departing from the concept of this invention, may result in less temperature uniformity within the sample. This is acceptable in some cases. The vertical thickness of the sample block is not critical, but it is advantageous for both the sample block and sample not to be too thick, to enable rapid stabilization of the temperature. In one embodiment, one or more ends of sample 18 probed by position sensors 14 and 16 are coated with a reflective film to increase reflection from the sample. The reflective film is made from a highly reflective material. Example reflective films include metals, such as aluminum, silver, or copper. In order to maintain accuracy of the measurement from sample 18, thermal effects from the reflective film need to be minimized. Thermal effects from the reflective film are negligible when the thickness of the reflective film is sufficiently small. The thickness of the reflective film is less than 100 nm, or less than 75 nm, or less than 50 nm, or less than 25 nm, or less than 15 nm, or in the range from 5 nm-100 nm, or in the range from 10 nm-75 nm, or in the range from 5 nm-50 nm, or in the range from 10 nm-50 nm.

In an alternative embodiment, the holder and the frame are machined out of the same solid piece of material. This embodiment is functionally equivalent to the one shown in FIG. 3B, does not depart from the spirit of this invention, but it is potentially more costly to build and affords less flexibility in adjusting the setup to different sample sizes. The sample holder can be provided in a number of shapes such as a solid block instead of U-shaped, without departing from the spirit of this invention. A solid shape is considered less advantageous, because it would increase the area of thermal contact between the sample and the holder, making it more difficult to control the sample temperature as it is swept through the measurement range, and also potentially inducing strong temperature gradients within the holder (and even the frame) due to the increased heat flow.

As depicted in FIG. 3B, the frame 12, sample holder 20 and sample block 22 configuration allow for effective control of the sample temperature over a reasonably wide temperature range (e.g., a range greater than 10K, 20K or 50K), such as between room temperature and 80° C., allowing for sufficient characterization of the thermal expansion of the sample. Since electrical connections are necessary in order to supply current to the block heaters as well as to read the temperature of the provided sensors, it is highly desirable that the electrical conductors are made of a fine gauge wire, and are placed such that they will not exert a sizable force on the sample plus sample block unit. In practical terms, since the area of contact between the holder and the sample is significantly smaller than all other contact areas (such as between frame and holder, and between sample and sample block), any significant amount of force applied by the heater and sensor wires will result in undesirable motion of the sample with respect to the measurement frame, resulting in potential degradation of measurement quality and, in extreme cases, failure of the measurement if the resulting sample rotation results in loss of the needed optical alignment between position sensors and sample ends.

In order to achieve maximum stability and measurement accuracy, the frame-holder setup is kept at a constant temperature while the sample temperature is swept through the measurement range of interest. A temperature controlled base 50 is provided with one or multiple heating elements 52, such as electrical heaters that supply thermal energy (heat) to the frame and sensors, and one or more temperature sensors 54, such as platinum resistance sensors or similar. A controller 56 is used to regulate the heater elements in response to measured temperature. The temperature of the frame and sensors is regulated over a very narrow range (e.g., <0.02 K or <0.01 K or <0.005 K). This base is preferably made of a high thermal conductivity material, such as aluminum or other metal, and provides solid mechanical support for the measurement frame, which is placed directly on top of the base. A layer of a viscous compound is preferably provided between the base and the measurement frame to improve thermal contact between the two. This thermal contact is maximized by providing a large area of contact between the base and the bottom of the measurement frame. The base holding the complete setup can be placed within a high vacuum enclosure, where air pressure is preferably kept below $10^{-6}$ bar by means of suitable, commercially available vacuum equipment. The vacuum enables independent temperature control of sample and frame, and eliminates position sensing errors due to air refractivity changes caused by variations in atmospheric conditions. The vacuum is not essential, and measurement accuracy can be preserved at a level acceptable for less critical measurements by providing compensation for atmospheric changes.

Thermal radiation shields can be provided between the sample and the position sensors, and between the measurement frame and sample holder, in order to minimize changes as the sample temperature is intentionally swept through the measurement range of interest. Similarly, additional radiation shields can be placed covering the exterior of the measurement setup, in order to prevent external temperature changes from inducing temperature changes within the setup. These radiation shields can be firmly attached to the base of the instrument, to ensure temperature uniformity throughout the setup.

Vibration isolation of the instrument with respect to the external environment can be provided. Since the instrument disclosed herein is quite compact and rigid, its demands for vibration isolation are less stringent than for other similar setups, and sufficient isolation has been achieved by mounting the base of the instrument onto a solid surface by means of inexpensive vibration-absorbing viscoelastic supports such as those supplied by Thorlabs Inc (Newton, N.J.), as part #AV5, made of "Sorbothane®". This material is also a poor thermal conductor, thus simultaneously providing thermal isolation between the instrument base and the external world. Although not strictly necessary, additional vibration isolation mechanisms, such as an optical table or active vibration cancellation could be provided to enable measurements in noisier environments without departing from the spirit of this invention. Supports made from other similar rubbery materials could be used instead of Sorbothane feet while staying within the scope of this invention.

The changes in length of the sample are recorded by high resolution position sensors. Suitable sensors and associated optical and electronic components are manufactured and commercialized by attocube systems AG under the name FPS Interferometric Sensors. These fiber-based interferometric sensors provide position detection with resolution at the pico-meter level with high measurement bandwidth into the MHz range. Although a thermal expansion measurement is not generally considered a fast measurement requiring high measurement bandwidth, the wide bandwidth is beneficial in helping to track and ultimately reject any possible vibration of the sample with respect to the measurement frame. The attocube sensor system includes an internal absolute wavelength reference which ensures high stability in the length measurements. Alternatively, multi-phase shift interferometric position sensors such as, or similar to, disclosed by Peale, Duran and Hess in U.S. Pat. No. 6,687,008 can also be used to this effect.

As shown in FIG. 3B, the changes in length of the sample can be determined by measuring the positions detected on each sample end by the two position sensors 14, 16, by subtracting the distances measured by them from the effective length of the measurement frame, which is in practice defined by the internal reference surfaces within each sensor. It will become apparent to those skilled in the art that the absolute distance is not known and not important for the measurement of the thermal expansion of the sample. However, since we are interested in detecting sub-nm level changes in the length of the sample, it is of primary importance that the effective length of the measurement frame remains fixed at a level of stability similar or better than the sample length changes to be measured, for the duration of the measurement. The attocube position sensors are made of metallic titanium, which is not a low thermal expansion material at room temperature. For this reason, even if the frame is made of ULE® glass and kept at the glass Tzc, small changes in the temperature of the frame will cause changes in the temperature of the sensors, which will dilate causing the effective length of the measurement frame to vary. This effect can be minimized by appropriately holding the sensors to seek "athermal" behavior. This can be accomplished by fixing the sensors to the frame at a plane perpendicular to the sensors optical axis such that the plane lies as close as possible to the location of the internal position reference in the sensors. The attocube sensors effectively use the tip of the incoming optical fiber as the reference surface for the position measurement. In the illustrated embodiment, the sensors are held on to the frame at a plane containing, or lying as close as practically possible to, the tip of the fiber connecting the sensor to the measurement system.

Figure 4:
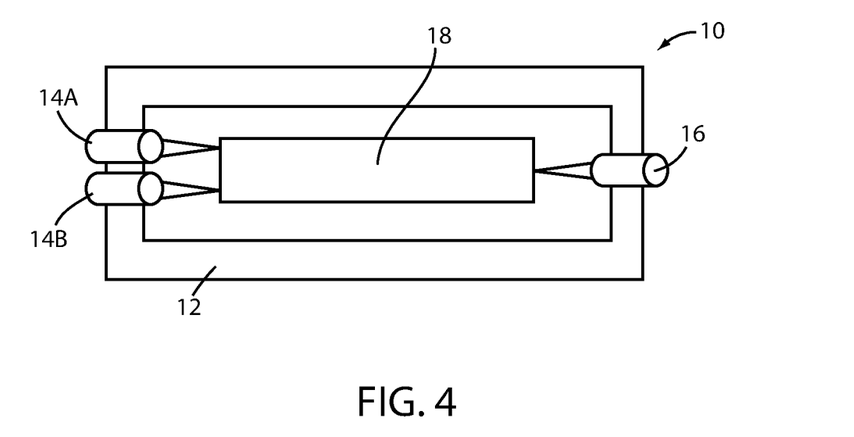
FIG. 4 is a schematic (omitting sample and frame temperature regulating means, vacuum chamber, and reflective shields) of an apparatus wherein the position sensors are held by a frame made of a low expansion material, such as ultralow expansion ULE® glass made by Corning Incorporated, or another ultralow expansion material and wherein dual sensors on one side allow detection of possible sample rotation about the axis deemed most susceptible to allow sample rotation.
Figure 5:
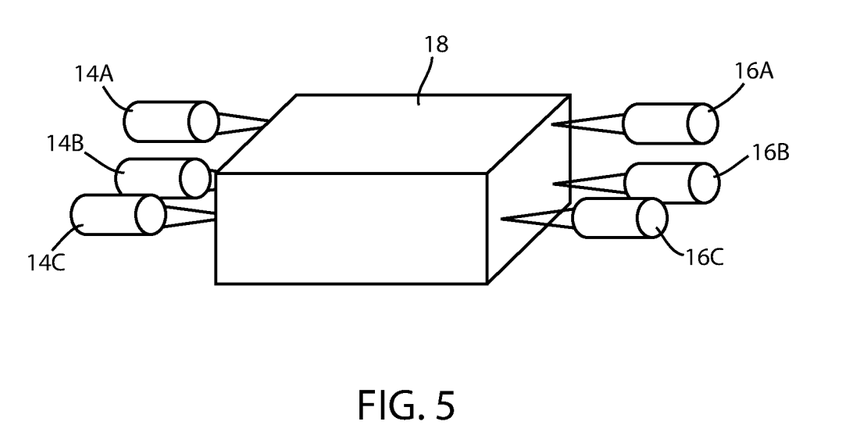
FIG. 5 is a schematic (omitting the frame, temperature regulator means, vacuum chamber and reflective shields) of the sensor arrangement of an embodiment including a set of three sensors on each sample end, which allows detection and correction of rotations around an arbitrary axis, and/or deformation of the sample caused by intrinsic non-uniformity.

FIG. 3B shows a standard implementation with two sensors 14, 16, each detecting the position of one of the two opposing ends of the sample being measured. This configuration works well for many measurements and in cases where there is no sample rotation. However, if the sample is allowed to rotate, changes in the sample angle may appear as changes in sample length. If the rotation takes place as the sample temperature is varied to record the thermal expansion, this effect can lead to erroneous determination of the sample expansivity. FIG. 4 shows an implementation, using three sensors 14A, 14B and 16 where two sensors are used for measuring the position of one of the sample ends and the remaining sensor measures the opposite end. This implementation is sufficient for the vast majority of cases, when the holder supports the sample from below, and thus likely motion of the sample is restricted to the horizontal plane. In this configuration, and in the case of samples that dilate uniformly without shape distortion, a co-planar arrangement of the three sensors in a horizontal plane is enough to detect, and if necessary, correct for rotations within the horizontal plane. FIG. 5 shows an embodiment using a total of six sensors 14A, 14B 14C, 16A, 16B and 16C, divided into two sets of three sensors, each set measuring points on each of the two end surfaces of the sample. By arranging each set to measure on non-collinear points on the sample surface rotations within arbitrary planes and/or sample distortions caused by sample non-uniformity can be detected. The data provided by the multiplicity of sensors can be then appropriately processed to extract more accurate thermal expansion data as well as some information on thermal expansion uniformity patterns.

Figure 6:
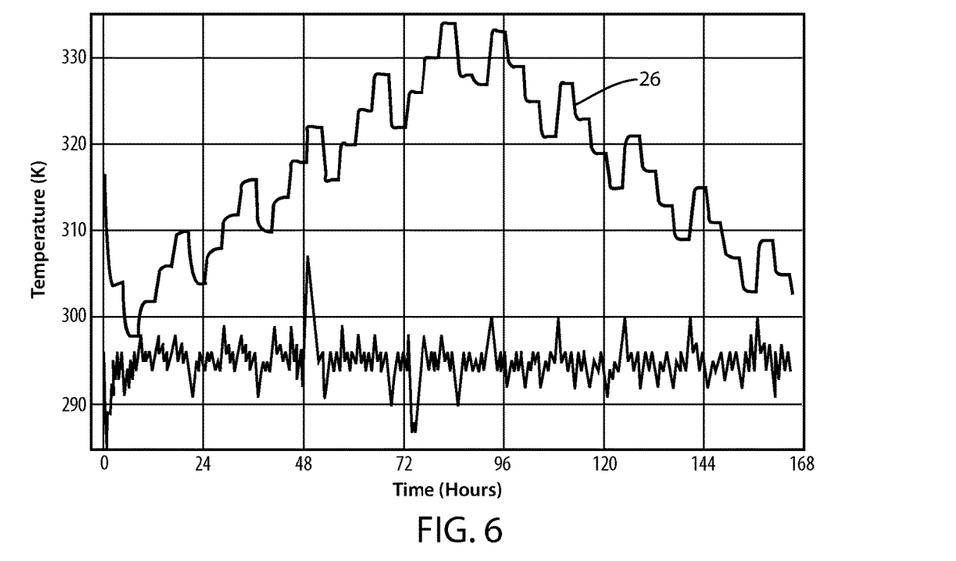
FIG. 6 is a graph showing time evolution of the sample temperature and the measurement frame temperature variations during a thermal expansion measurement, in which the units apply to the sample temperature, which changes between 298 K and 334 K, and wherein the frame temperature differences have been multiplied by 1000×, meaning that the large excursion event at t=~48 hours has a peak amplitude of about 12 mK.

FIG. 6 shows temperature data collected during a thermal expansion measurement experiment performed on a sample of ULE® glass using the apparatus described herein. The sample temperature (represented by curve 26) is measured by means of a commercial Pt resistor mounted on a "sample block", made of aluminum and placed on top and in close contact with the sample. A thin layer of a heat conductive paste or grease is used between the sample and the block to promote intimate thermal contact without the block stressing the sample or impeding in any way its dilation. An electrical heater is also mounted on the aluminum sample block in order to allow heating of the sample and thermal regulation within a suitable temperature range. The sample temperature is regulated at a series of set points, which in this case are changed automatically, such as every 4 hours by a computer that controls the experiment and collects the data. This time was determined as sufficiently long to allow thermal stabilization of the sample. Measurements can be carried out at a faster pace without detrimental effects on the final results. It is clear to those skilled in the art of thermal measurements that modifications to temperature control parameters, adjustments to the sample and sample block dimensions and material can be used to optimize thermalization times in order to make the measurement faster and/or more accurate, without departing from the spirit of this invention.

In FIG. 6, it can be seen that the temperature is not changed monotonically from low to high set points or from high to low, but rather the sequence of set points is chosen so that short series of increasing temperature set points are followed by a lower set point, from which a new series of increasing set points initiates. For example, at time equal 48 hours, the temperature had been set to 322 K, held for 4 hours, and at time equal to 52 hrs, it was brought down to 316 K. After 4 hours at that point, the set point was changed successively to 320 K, 324 K, and 328 K, after which it was brought back to 322 K at time equal to 68 hours. This algorithm results on a "mini-ramp" being bracketed by two measurements at the same intermediate temperature. Since thermal expansion in ULE® glass and most other materials is known to be reversible, this data allows measuring any instrument drift that may have taken place. Upon return to the same temperature, the sample acquires the same length, and drift correction is carried out by interpolating the measured drift at the times of the acquisition of the different lengths in the "mini-ramp", i.e., 316, 320, 324 and 328 K, and applying the corrections to each point. By suitably choosing the set points, the correction can be carried out with only a small throughput penalty, since the two measurements at 316 K are used as part of other measurement "mini-ramps". The procedure is carried successively for all mini ramps, resulting in a final data set which has been corrected from drifts. It will become clear to those skilled in the art that a number of variations can be applied to this algorithm, and that success of such algorithms substantially depends on measurement drift being slow enough and small in amplitude compared to measurement times and changes in length associated with the sample and the temperature range being covered. It is also generally recognized that success of this class of recurrent correction algorithms also depends on measurement noise being low enough in order to avoid accumulation of errors during the correction process. It has been found that it is generally necessary to acquire sample length data with noise generally below 0.3 nm in order to achieve the desired precision and accuracy in the final result.

Without departing from the spirit of the invention, for example, the number of points within a "mini-ramp" can be reduced or expanded, depending on accuracy need and level of drift in the instrument. After reaching a maximum temperature of 334 K at time equal 80 hours, and acquiring data at an extra set point of 328 K for drift correction purposes, the procedure is repeated for decreasing temperature set points, which are interleaved with those acquired while temperature was increased in the first part of the experiment. This decreasing ramp adds measurement points to enhance overall accuracy, and can therefore be partially or completely omitted in order to save measurement time, without departing from the essence of this invention.

FIG. 6 also shows, in a vertical scale that has been expanded by a factor of 1000, the relative temperature variations measured at a point on the measurement frame by means of a separate Pt thermometer. The location of that thermometer was chosen in this case to be close to one of the position sensors, in order for it to closely reflect temperature changes that can have the most detrimental effect on the measurement. That thermometer was used in a second temperature control loop, including a second electrical heater (identified as 52 in FIG. 3B) that was used to maintain the frame temperature as constant as possible throughout the week-long measurement. The frame temperature can be observed to have remained stable within ±5 mK most of the time, with the exception of two environmentally-induced events at times ~48 hr and ~74 hr, when there were excursions of ~12 mK and 8 mK, respectively. These events have detrimental effects on the measurement that can be observed on the position measurements in FIG. 8, and on the calculated length changes in FIGS. 9 and 10. In particular, the point at T equal 53° C. still shows as an outlier, despite the adjustment illustrated in FIG. 8. This adjustment procedure consists of compensating the position measurements when excursions are observed in the frame temperature. This is achieved by a previous calibration of the effect of a frame temperature excursion on the detector readings, while the sample is kept at a constant temperature. The correction reduces the impact of excursion events to varying degrees of success, depending on the intensity and duration of the excursion, but generally some distortions persist after the correction. As stated above, these excursions are due to changes in temperature external to the experiment itself, which affect the heat exchange between the setup and the environment. Excursions can be eliminated by placing the measurement setup in a metrology room, where the room temperature is kept within a narrow range, typically a fraction of a degree Celsius (1° C.). An alternative is to enclose the setup within an additional set of thermal shields placed inside the chamber, whose temperature is potentially controlled as well by means of an additional control loop. Although less desirable due to its impact in system size, cost and compactness, such solution would not represent a departure from the spirit of the invention disclosed herein.

Figure 7:
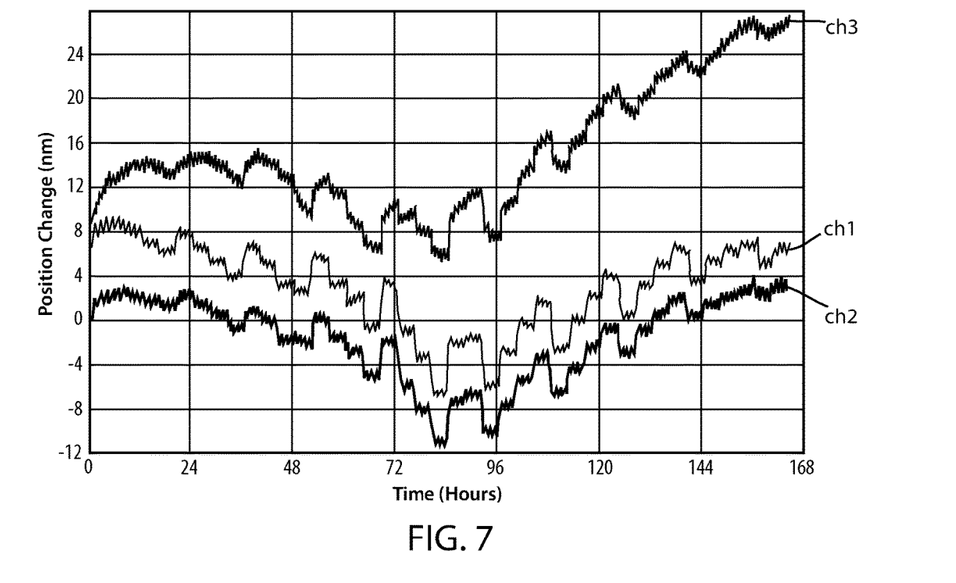
FIG. 7 is a graph showing relative position measurements (in nm) measured by three detectors mounted in a configuration as shown in FIG. 4, in which sensor channels Ch1 and Ch 2 are measured on the left side of the sample, while the sensor channel Ch 3 is measured on the right side of the sample, and positions are referenced to zero at a convenient time of the measurement process. The curves have been vertically displaced for clarity.

FIG. 7 shows the raw position measurements detected by the three sensors, identified as Ch 1, Ch 2 and Ch 3. Ch 1 and Ch 2 measure position of the left end of the sample, while Ch 3 measured position of the right side. The traces in the graph have been vertically displaced by arbitrary offsets in order to enable better visibility of the data, and appear in the order Ch 2, Ch 1, Ch 3 from the bottom of the graph. It can be seen that steps in positions measured by Ch 1 and 2 closely reflect the sample temperature changes in FIG. 6. Ch 3 also follows the trend, but it is clear that there is significantly higher drift in the latter case, amounting to about 20 nm accumulated over the week-long experiment. This drift, however, can be seen to be slow and steady, and thus subject to correction by means of an algorithm as discussed above. It should be noted that generally the use of such algorithms needs to be decided beforehand, in order for the data to contain enough redundancy that the correction algorithm can be successfully applied to the final data.

Figure 8:
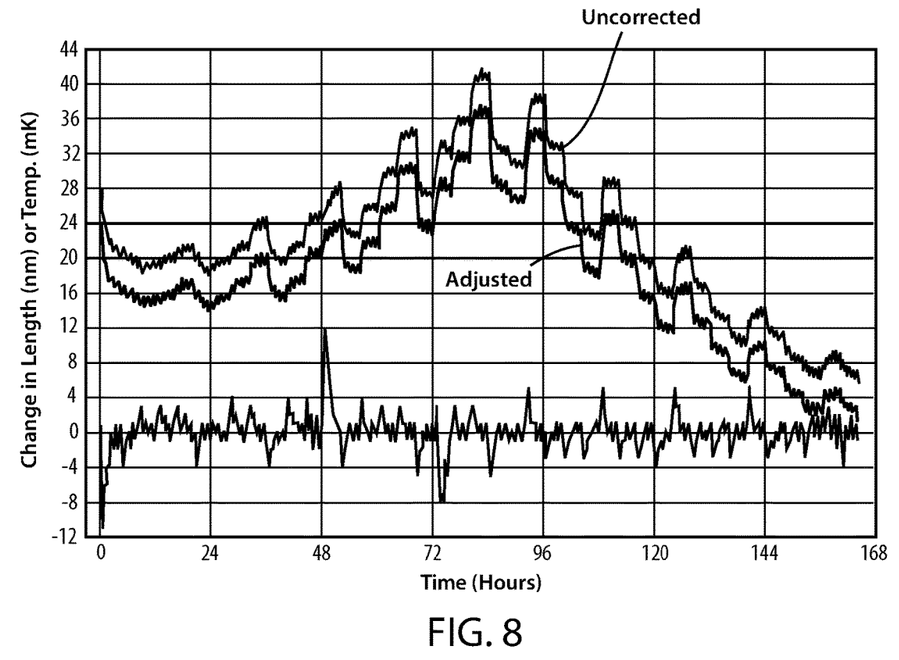
FIG. 8 is a graph showing change in sample length calculated from the measurements in FIG. 7, wherein a positive change indicates the sample is becoming longer, wherein the curve at the bottom indicates changes in the measured frame temperature, "uncorrected" is the uncorrected length data, and "adjusted" is the uncorrected length data after adjustment for frame temperature excursions. The curves have been displaced vertically for clarity.

FIG. 8 shows the sample length change over time, calculated by simply combining the three channel measurements using $\Delta L = -(Ch\ 3 + (Ch\ 1 + Ch\ 2)/2)$.

The adjusted trace in FIG. 8 would almost completely obscure the uncorrected trace which corresponds to the raw lengths calculated with the expression above, so it has been displaced down by 4 nm in order to make both traces visible. The adjustment process attempts to reduce the impact of thermal frame excursions such as the events at time ~48 hr and 74 hr. This data is not corrected for drift, as can be seen by comparing measured lengths at similar temperatures at the beginning and at the end of the experiment. Near the bottom of FIG. 8 we reproduce the frame temperature trace previously displaced in FIG. 6, in order to highlight the correlation between the temperature excursions and differences between the length data before and after adjustment.

Figure 9:
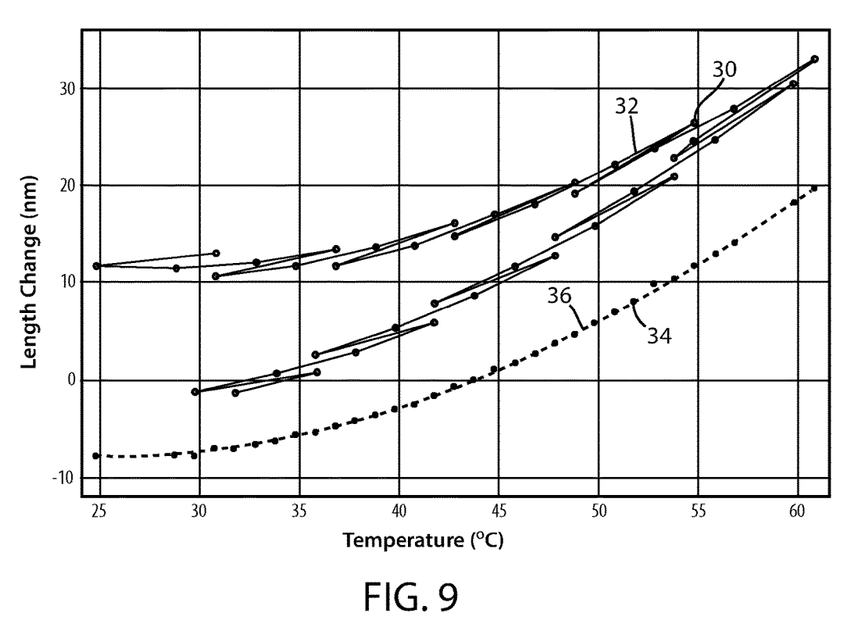
FIG. 9 is a graph showing length change vs. temperature, obtained by combining the data from FIGS. 6 and 8, wherein the connected squares indicate the adjusted uncorrected sample length, containing errors due to nm-level drift that accumulates along the measurement and the circles represent those same measurements after correction using an algorithm to measure and remove the drift with the dashed line indicating the expected behavior for ULE® glass with CTE=−9.5 ppb/K at 20° C., and standard temperature dependence with a CTE slope=1.58 ppb/K$^2$ at 20° C.

FIG. 9 plots the length data as a function of temperature. This is done by combining the temperature data in FIG. 6 with the length data in FIG. 8. Since at each temperature step there is a transition period during which the sample temperature is changing, the data in FIG. 9 is calculated by averaging the temperature and position readings acquired during the last hour at each set point. The fraction of data ultimately used can be changed without departing from the spirit of the invention. It is generally obvious that faster stabilization would allow an earlier start of the acquisition of useful data, better accuracy through more averaging and/or faster measurements through shorter hold times at each set point. The connected open circles 30 in FIG. 9 show the uncorrected data, and the effects of drift. The line 32 joining the points highlights the continuity of the drift process. The dots 34 represent the data from the open circles 30, after the drift correction algorithm was applied. The corrected data has been vertically displaced by a constant offset in order to improve graph visibility. Notice that application of this algorithm has little or no effect on the increased error on the point measured at T equals ~53° C., whose increased error is associated with the frame excursion event at 74 hours into the measurement.

The drift correction algorithm is highly successful, as illustrated by the fact that the data points 34 in FIG. 9 closely follow the expected thermal expansion behavior for this sample, illustrated by the fit line that runs through them. From the parameters used to generate this line, we conclude that the CTE at 20° C. for this glass sample is −9.5 ppb/K, with the expected CTE slope of 1.58 ppb/K$^2$ at that same temperature.

Figure 10:
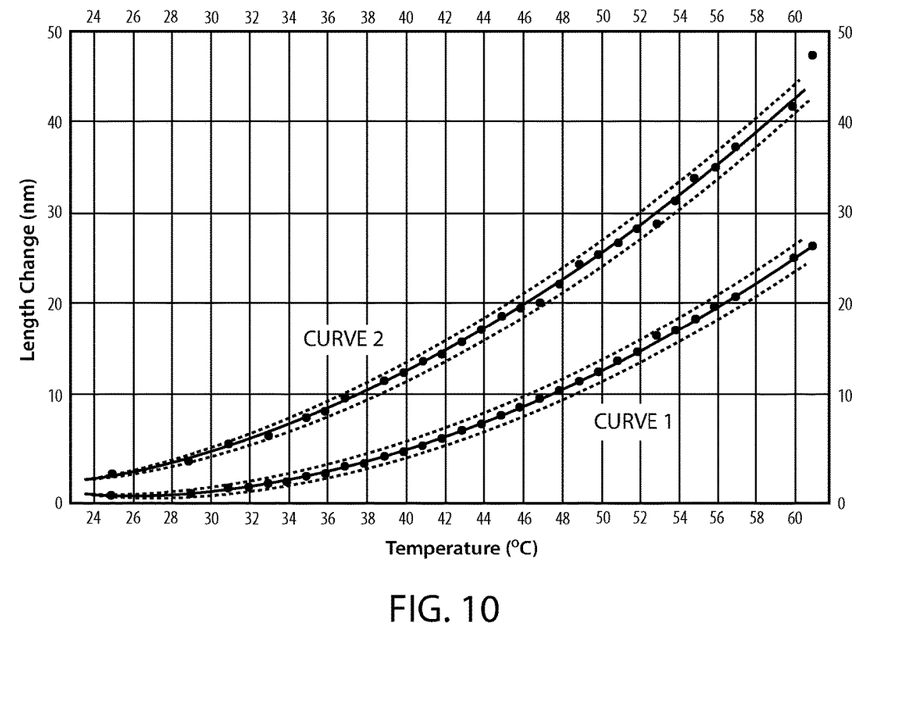
FIG. 10 is a graph showing corrected values for length change versus temperature for two different ULE® samples, in which Curve 1 shows the same data as in FIG. 9, and Curve 2 shows the results from a different sample, wherein the solid line is calculated for standard ULE® with CTE=1.5 ppb/K at 20° C. and CTE slope=1.6 ppb/K$^2$ at 20° C., the difference in CTE at 20° C. between the two samples had been measured using the sandwich seal technique and found to be between 11 and 14 ppb/K, and the dotted lines indicate error bars at ±1 ppb/K from the solid lines, highlighting the resolution at the $10^{-9}$/° C. level achieved by the disclosed method and apparatus.

FIG. 10 compares the corrected data from FIG. 9 (curve 1) with similar data acquired on a different sample of ULE® glass (curve 2). During the acquisition of this second set of data, there was a relatively long period of time during which the frame temperature was unregulated and drifted as much as 200 mK away from the target. This resulted in a number of data points with increased error. Despite this, the CTE of this sample is clearly observed to be distinct from the previous measurement, and we arrive at a CTE=1.5 ppb/K at 20° C. based on the solid line fitted through the data.

The dashed lines in FIG. 10 illustrate error bars of ±1 ppb/K from the best estimate lines for each of the two sets of data. It is clear that in both cases, the error estimates contain enough of the data points that the technique can be considered to resolve differences in CTE in the order or better than 1 ppb/K, or $10^{-9}$/° C.

Table 1 is a collection of measurements on a set of samples measuring 38 mm in length (25 mm wide, 3.55 mm thick) using the apparatus described herein. The data show that this system is capable of establishing absolute CTE with a maximum error of +/−2 ppb/K. The average of all the errors is significantly less than 1 ppb/K, indicating that the precision of the measurement is 2 ppb/K, and the accuracy better than 0.5 ppb/K, on samples weighing ~7 grams each. The system can also measure the slope of the CTE(T) curve with a precision of 0.1 ppb/K$^2$, on the same samples. The errors in slope and absolute CTE are correlated, and they partially compensate when the Tzc is calculated, so the data shows a precision of about 1° C. for Tzc, with accuracy better than 0.5° C.

The data in Table 1 summarizes measurements carried out on the same apparatus as the one used to gather the data in FIGS. 6 through 10, but after tuning and improvements that resulted in better temperature control of both sample and measurement frame. The system was placed in a temperature regulated room, and thus excursions such as the events at 48 and 72 hours were eliminated. Also, better tuning of the frame temperature control parameters, and reduction in the step amplitude during sample temperature changes allowed maintaining the frame temperature within a very narrow range of 0.005 K. Sample temperature control was also improved, allowing temperature stabilization of the sample after each step in only a few minutes, allowing much faster data acquisition. Thus, holding time at each temperature was reduced to about 20 minutes at each measurement point, compared to the 4 hours per point shown in FIG. 6. Each full-range independent CTE measurement entered as a line in Table 1 was measured in a period of 20 to 24 hours, or about one day, instead of the 7 days taken to acquire the data in FIGS. 6-10. This demonstrates the ability of this invention to carry out highly precise and accurate thermal expansion measurements much faster than any high-resolution custom-made dilatometers costing several times as much.

Certain custom-made dilatometers provide better accuracy than the disclosed apparatus. For example, the FPI dilatometer measures Tzc with precision and accuracy around or better than 0.3° C. But making a suitable sample requires more than 100 grams of material, and takes several weeks. The cost of machining the sample is up to 10× higher ($1,500 per sample), the measurement takes 3× longer to make, on a system that is in the order of 3× more expensive. When all factors are included, the cost of a measurement on the disclosed system is estimated to be ~20× less expensive than for the FPI dilatometer. The "turn-around" time, from the moment the material is ready for measurement to data availability, including sample preparation time, is about 4× faster (2 weeks instead of 8 weeks). These savings are very significant in the context of a manufacturing operation, allowing for a significantly more streamlined production and quality control process.

TABLE 1

| Sample | Expected | | | CHRD Measurements | | | | | | |
|---|---|---|---|---|---|---|---|---|---|---|
| ID | CTE20 | Slope20 | Tzc | RunID | Orient | fitCTE | ΔCTE | fitSlope | Tzc | ΔTzc |
| 70A | −7 | 1.51 | 24.80 | 3a | Std | −6.90 | 0.10 | 1.468 | 24.87 | 0.07 |
| 70A | −7 | 1.51 | 24.80 | 3b | Std | −6.87 | 0.13 | 1.443 | 24.94 | 0.14 |
| 70A | −7 | 1.51 | 24.80 | 3c | Std | −6.36 | 0.64 | 1.456 | 24.52 | −0.28 |
| 70A | −7 | 1.51 | 24.80 | 4a | Q4 | −8.32 | −1.32 | 1.481 | 25.86 | 1.07 |
| 70A | −7 | 1.51 | 24.80 | 4b | Q4 | −7.58 | −0.58 | 1.455 | 25.42 | 0.63 |
| 70A | −7 | 1.51 | 24.80 | 4c | Q4 | −5.52 | 1.48 | 1.412 | 24.03 | −0.77 |
| 70A | −7 | 1.51 | 24.80 | 5a | Std | −7.09 | −0.09 | 1.491 | 24.93 | 0.13 |
| 71B | −24.7 | 1.59 | 37.57 | 3a | Std | −25.66 | −0.96 | 1.613 | 38.02 | 0.45 |
| 71B | −24.7 | 1.59 | 37.57 | 3b | Std | −26.14 | −1.44 | 1.601 | 38.60 | 1.02 |
| 71B | −24.7 | 1.59 | 37.57 | 4a | Q4 | −25.91 | −1.21 | 1.638 | 37.86 | 0.29 |
| 71B | −24.7 | 1.59 | 37.57 | 5a | Std | −23.43 | 1.27 | 1.515 | 37.62 | 0.04 |
| 71B | −24.7 | 1.59 | 37.57 | 5b | Std | −24.22 | 0.48 | 1.545 | 37.84 | 0.26 |
| 71B | −24.7 | 1.59 | 37.57 | 5c | Std | −23.72 | 0.98 | 1.538 | 37.52 | −0.06 |
| 71C | −24.7 | 1.59 | 37.57 | 3a | Std | −23.91 | 0.79 | 1.508 | 38.15 | 0.57 |
| 71C | −24.7 | 1.59 | 37.57 | 3b | Std | −24.35 | 0.35 | 1.51 | 38.51 | 0.93 |
| 71C | −24.7 | 1.59 | 37.57 | 3c | Std | −24.2 | 0.5 | 1.517 | 38.26 | 0.69 |
| 71C | −24.7 | 1.59 | 37.57 | 3d | Std | −23.45 | 1.25 | 1.499 | 37.88 | 0.31 |

TABLE 1-continued

| | | | | | | | | | | |
|---|---|---|---|---|---|---|---|---|---|---|
| 71C | −24.7 | 1.59 | 37.57 | 3e | Std | −22.7 | 2 | 1.499 | 37.22 | −0.35 |
| 72B | −17 | 1.59 | 31.58 | 3a | Std | −17.32 | −0.32 | 1.537 | 32.30 | 0.73 |
| 72B | −17 | 1.59 | 31.58 | 3b | Std | −17.08 | −0.08 | 1.502 | 32.46 | 0.88 |
| 72C | −17 | 1.59 | 31.58 | 3a | Std | −17.75 | −0.75 | 1.542 | 32.59 | 1.01 |
| 72C | −17 | 1.59 | 31.58 | 3b | Std | −18.25 | −1.25 | 1.549 | 32.91 | 1.34 |
| 73B | −10.6 | 1.61 | 26.89 | 3a | Std | −9.9 | 0.7 | 1.535 | 26.76 | −0.13 |
| 73B | −10.6 | 1.61 | 26.89 | 3b | Std | −11.8 | −1.2 | 1.587 | 27.84 | 0.95 |
| 73C | −10.6 | 1.61 | 26.89 | 3a | Std | −11.12 | −0.52 | 1.606 | 27.27 | 0.38 |
| 73C | −10.6 | 1.61 | 26.89 | 3b | Std | −11.36 | −0.76 | 1.622 | 27.35 | 0.46 |
| 73C | −10.6 | 1.61 | 26.89 | 3c | Std | −10.44 | 0.16 | 1.612 | 26.78 | −0.12 |
| 73C | −10.6 | 1.61 | 26.89 | 3d | Std | −10.53 | 0.07 | 1.615 | 26.82 | −0.07 |
| 74B | −21 | 1.59 | 34.62 | 3a | Std | −19.77 | 1.23 | 1.564 | 33.95 | −0.67 |
| 74B | −21 | 1.59 | 34.62 | 3b | Std | −21.61 | −0.61 | 1.596 | 35.03 | 0.41 |
| 75B | −12.6 | 1.59 | 28.39 | 3 | Std | −12.45 | 0.15 | 1.610 | 28.17 | −0.22 |
| 76B | −12.8 | 1.65 | 28.18 | 3 | Std | −12.24 | 0.56 | 1.637 | 27.87 | −0.31 |
| 81117B | 0.75 | 1.60 | 19.53 | 1a | Std | −1.35 | −2.1 | 1.663 | 20.82 | 1.28 |

MAXIMUM ERROR ON ALL SAMPLES

| | ΔCTE | ΔTzc |
|---|---|---|
| Max | 2.00 | 1.34 |
| Min | −2.10 | −0.77 |

The methods disclosed herein can be used for measuring the coefficient of thermal expansion of a sample of a material having a weight less than 50 grams or a volume less than 25 cubic centimeters, or a length less than 100 millimeters to a precision (or standard deviation) that is no greater (i.e., better) than 10 ppb/K, 5 ppb/K, or 3 ppb/K. As used herein, the term "precision" is used to denote a measure of statistical variability attributable to random errors, and is related to reproducibility and repeatability. More specifically, as used herein, the term "precision" is the experimental standard deviation. Accuracy refers to the closeness of a measured value to the true value, and could, in theory coincide with precision when a method and measuring apparatus are perfectly calibrated.

The described embodiments are preferred and/or illustrative, but are not limiting. Various modifications are considered within the purview and scope of the appended claims.

What is claimed is:

1. A process for determining an absolute coefficient of thermal expansion in a sample, comprising:
    supporting a sample on a frame, the sample having a first boundary opposite a second boundary, the frame having a first end opposite a second end, the frame supporting at least one optical sensor on the first end and at least one optical sensor on the second end, the at least one optical sensor supported on the first end directing an optical signal at the first boundary of the sample, the at least one optical sensor supported on the second end directing an optical signal at the second boundary of the sample;
    regulating the temperature of the frame within a first range that is within ±0.02 K of a frame set point temperature;
    varying the temperature of the sample over a second range that is greater than 1K while maintaining the temperature of the frame within the first range;
    measuring the change in length of the sample as a function of temperature over the second range; and
    determining the absolute coefficient of thermal expansion based on the measured change in length of the sample as a function of temperature.

2. The process of claim 1, wherein the frame comprises a frame material having a Tzc and the temperature of the frame is maintained within a temperature range of about ±0.01° C. of a frame set point temperature, the frame set point temperature being within about ±5° C. of the Tzc of the frame material.

3. The process of claim 1, wherein the frame comprises a frame material having a Tzc and the temperature of the frame is maintained within a temperature range of about 0.005° C. of a frame set point temperature, the frame set point temperature being within about ±2° C. of the Tzc of the frame material.

4. The process of claim 1, wherein the second range extends over at least 25 K and the measuring is completed within a period of 24 hours.

5. The process of claim 1, wherein the temperature of the sample is varied non-monotonically.

6. The process in claim 5, wherein the varying sample temperature includes a plurality of temperature steps, each of the sample temperature steps having a fixed sample temperature and including a hold time at the fixed sample temperature.

7. The process of claim 1, wherein the first boundary of the sample is coated with a reflective film.

8. The process of claim 7, wherein the reflective film comprises Al.

9. The process of claim 7, wherein the thickness of the reflective film is less than 50 nm.

10. A method of determining the coefficient of thermal expansion of a sample of a material, comprising: supporting a sample on a frame, the sample having a first boundary opposite a second boundary, the frame having a first end opposite a second end, the frame supporting at least one optical sensor on the first end and at least one optical sensor on the second end, the at least one optical sensor supported on the first end directing an optical signal at the first boundary of the sample, the at least one optical sensor supported on the second end directing an optical signal at the second boundary of the sample;
    regulating the temperature of the frame within a first range that is within ±0.02 K of a set point temperature;
    varying the temperature of the sample over a second range that is greater than 1K while maintaining the temperature of the frame within the first range;
    measuring the change in length of the sample as a function of temperature over the second range; and
    determining the absolute coefficient of thermal expansion based on the measured change in length of the sample as a function of temperature.

11. The method of claim 10, wherein the sample has a weight less than 50 grams, and the precision of the measurement is no greater than 10 ppb/K.

12. The method of claim 11, wherein the sample has a volume less than 25 cubic centimeters.

* * * * *

UNITED STATES PATENT AND TRADEMARK OFFICE
CERTIFICATE OF CORRECTION

PATENT NO. : 10,458,936 B2  
APPLICATION NO. : 15/493944  
DATED : October 29, 2019  
INVENTOR(S) : Carlos Alberto Duran

Page 1 of 1

It is certified that error appears in the above-identified patent and that said Letters Patent is hereby corrected as shown below:

In the Claims

In Column 18, Line 36, Claim 6, delete "process in claim" and insert -- process of claim --, therefor.

Signed and Sealed this
Eighteenth Day of February, 2020

Andrei Iancu
*Director of the United States Patent and Trademark Office*